US005575382A

United States Patent [19]
Sobel et al.

[11] Patent Number: 5,575,382
[45] Date of Patent: Nov. 19, 1996

[54] ROTARY SELF-WINDING TWO-PIECE LIGATURE PACKAGE

[75] Inventors: Martin Sobel, Flemington, N.J.; Robert J. Cerwin, Tipersville, Pa.

[73] Assignee: Ethicon, Inc., Somerville, N.J.

[21] Appl. No.: 362,681

[22] Filed: Dec. 22, 1994

[51] Int. Cl.⁶ .................................................. A61B 17/06
[52] U.S. Cl. .......................... 206/63.3; 206/380; 242/129
[58] Field of Search ............................... 206/63.3, 339, 206/380; 242/137, 137.1, 138, 141, 146, 129, 159, 164, 170

[56] References Cited

U.S. PATENT DOCUMENTS

| | | | |
|---|---|---|---|
| 2,615,565 | 1/1947 | Bower et al. | 206/63.3 |
| 3,648,949 | 3/1972 | Berger et al. | 242/159 |
| 3,972,418 | 8/1976 | Schuler et al. | 206/63.3 |
| 4,424,898 | 1/1984 | Thyen et al. | 206/63.3 |
| 4,961,498 | 10/1990 | Kalinski et al. | 206/339 |
| 4,967,902 | 11/1990 | Sobel et al. | 206/63.3 |
| 5,052,551 | 10/1991 | Cerwin et al. | 206/63.3 |
| 5,099,994 | 3/1992 | Kalinski et al. | 206/409 |
| 5,131,534 | 7/1992 | Brown et al. | 206/63.3 |
| 5,213,210 | 5/1993 | Cascio et al. | 206/380 |
| 5,228,565 | 7/1993 | Sinn | 206/63.3 |
| 5,249,671 | 10/1993 | Sinn | 206/63.6 |
| 5,407,071 | 4/1995 | Lawhon et al. | 206/63.3 X |

FOREIGN PATENT DOCUMENTS

| 1195425 | 11/1959 | France . |
|---|---|---|
| 1574869 | 7/1969 | France . |

*Primary Examiner*—Jacob K. Ackun
*Attorney, Agent, or Firm*—Hal Brent Woodrow

[57] ABSTRACT

A package for retaining at least one ligature comprising a circular plate having a circular recessed base in the central portion thereof and a raised outer perimeter forming an inner wall that extends from and is substantially perpendicular to the base and an upper ring that extends from the inner wall and is substantially perpendicular to the inner wall and extends away from the base; and a flange member having a lower ring with an outer edge and an inner edge, extending from the outer edge is an outer wall which is substantially perpendicular to the lower ring, the outer wall having a top, extending form the top is an outer member that is substantially perpendicularly to the outer wall and extends away from the lower ring wherein the inner wall of the circular plate fits inside the inner edge of the lower ring and is adjacent thereto and the combination of the inner wall, lower ring, the outer wall and the upper ring defines a channel suitable for retaining a ligature said channel having an aperture for receiving said ligature. A method of loading a suture armed with a needle in the package is also disclosed.

13 Claims, 3 Drawing Sheets

5,575,382

ROTARY SELF-WINDING TWO-PIECE LIGATURE PACKAGE

FIELD OF INVENTION

This invention relates to a ligature package and more specifically to a suture package designed to facilitate automatic loading of a needle and suture into said package.

BACKGROUND OF THE INVENTION

In packaging ligatures (such as sutures attached to needles) it is important that the needle and suture be provided in convenient economical packaging. The package must provide easy access to the needles and the needle and attached suture should withdraw from the package without binding or snagging. The package for manufacturing purpose should be easy to make and assemble and preferably be adapted to automated loading and assembly.

It is further desirable for suture packages to be economical to manufacture and assemble in large volumes. Suture packages toward this end are preferably made of molded, stamped or thermoformed polymeric materials. Additionally, it is highly desirable if the manufacturing process directed towards assembling and loading the suture package can be performed in a single automated process.

SUMMARY OF THE INVENTION

I have discovered a package for retaining at least one ligature comprising a circular plate having a circular recessed base in the central portion thereof and a raised outer perimeter forming an inner wall that extends from and is substantially perpendicular to the base and an upper ring that extends from and is substantially perpendicular to the inner wall and extends away from the base; and a flange member having a lower ring with an outer edge and an inner edge, extending from the outer edge is an outer wall which is substantially perpendicular to the lower ring, the outer wall having a top, extending form the top is an outer member that extends from and is substantially perpendicularly to the outer wall away from the lower ring wherein the inner wall of the circular plate fits inside the inner edge of the lower ring and is adjacent thereto and the combination of the inner wall, lower ring, the outer wall and the upper ring defines a channel suitable for retaining a ligature said channel having an aperture for receiving said ligature.

DESCRIPTION OF THE FIGURES

FIG. 3a illustrates two armed sutures secured in the needle park and the suture being placed across the winding slot. FIG. 3b illustrates the registry of the outer flange member with the inner circular plate so that an enclosed channel is formed between the inner and outer members. FIG. 3c illustrates the loading of the suture into the organizer by the rotation of the inner circular plate with respect to the flange member.

DETAILED DESCRIPTION OF THE INVENTION

Figure 1:
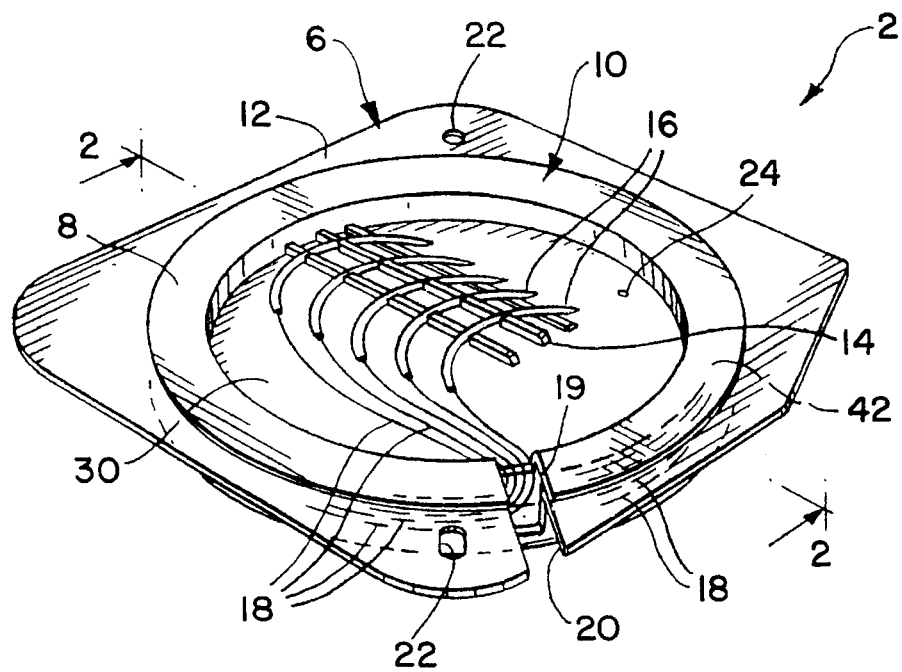
FIG. 1 is a perspective view of a ligature package according to a preferred embodiment of this invention.
Figure 2:
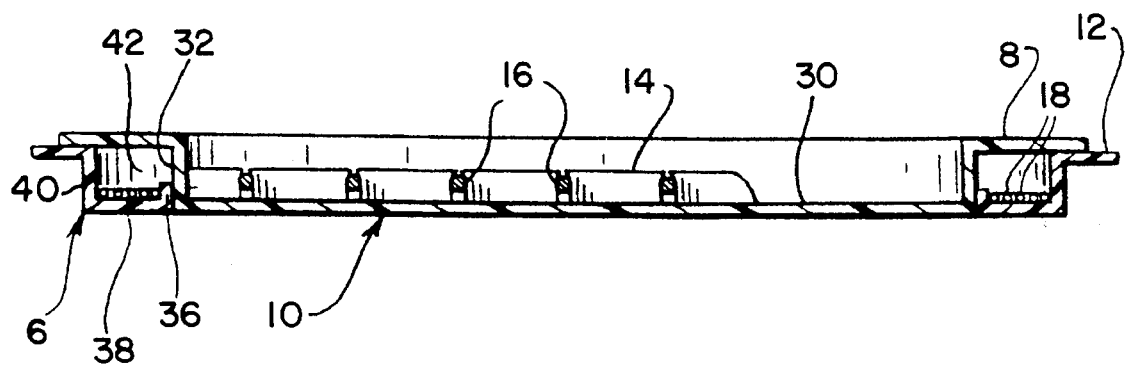
FIG. 2 is an enlarged cross-sectional view taken along line 2—2 of FIG. 1.

FIG. 1, illustrates a perspective view of the ligature package 2 of the present invention. FIG. 2 is an enlarged cross-sectional view of the ligature package. The ligature package 2 comprises a circular plate 10 and a flange member 6. The circular plate 10 has a circular recessed area in the center of the plate that form a base 30. The base 30 generally will have a means to secure one end of a ligature (such as suture 18) to the base 30. When a needle 16 has been attached to the suture 18, a needle park 14 may be employed to secure the needle and suture to the base 30. Many needle parks have been described in the prior art that would be suitable for mounting on the base 30 including but not limited to the needle parks described in U.S. Pat. Nos. 4,424,898, 5,099,994 and 5,213,210 which are hereby incorporated herein by reference. The base 30 may also have engagement means 24 to facilitate the mechanical handling of the circular plate 10. Extending from the base 30 along it perimeter is inner wall 32. The inner wall 32 extends substantially perpendicular to the plane of the base 30. Extending from the top of the inner wall 32 is upper ring 8 that is substantially perpendicular to the inner wall 32 and extends away from the base 30.

The flange member 6, as illustrated in FIG. 2, comprises a lower ring 38 having an inner and outer edge. Extending from the outer edge of the lower ring 38 is an outer wall 40, which is substantially perpendicularly to the lower ring 38. Extending from the top of the outer wall 40 is an outer member 12. Optionally a lip 36 may extend from the inner edge of the lower ring 38. The lip 36 as shown in FIG. 2 extends perpendicularly from the lower ring 38 on the same side of the lower ring as the outer wall 40.

The inner wall 32 of the circular plate 10 fits inside the lower ring 38 of the flange member 6. The inner wall 32 is in contact with the inner edge of the lower ring 38, unless lip 36 is present in which instance the inner wall will be in contact with the lip 36. The combination of the inner wall 32, the lower ring 38, the outer wall 40, the upper ring 8 and optionally the lip 36 defines a channel 42.

Extending substantially perpendicular from the top of the outer wall 40 is the outer member 12 of the flange member 6. The outer member 12 of the flange 6 provides the shape of the suture package's perimeter. Suture package 2 generally has a rectangular shape although the corners may be rounded or truncated for handling and package over wrapping purposes. The outer member 12 may also have at least one and preferably at least two engagement means 22 to facilitate the handling and loading of sutures within the ligature package 2. Additionally an aperture will generally be present in outer member 12 and/or in the base 30 of the circular plate 10 to allow the ligature to be wound into suture channel 42. As is illustrated, in one embodiment of the present invention, the winding slot 20 in the outer member and the channel access port 19 in the upper ring of the circular plate provide a path for the suture 18 to enter the channel 42 of the ligature package 2. The channel access port 19 may also provide an opening from the channel 42 into the base 30.

Figure 3A:
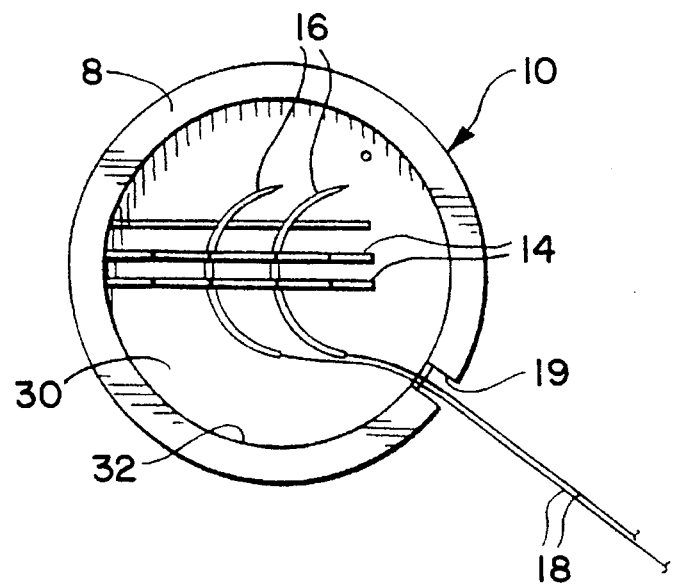
FIGS. 3a–c demonstrate the loading of two armed sutures in the suture organizer.
Figure 3B:
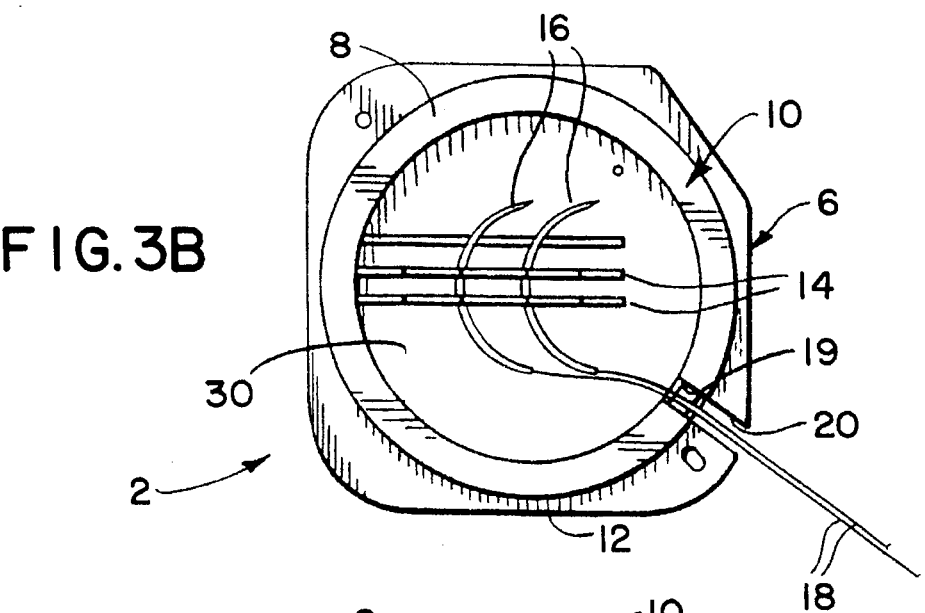
Figure 3C:
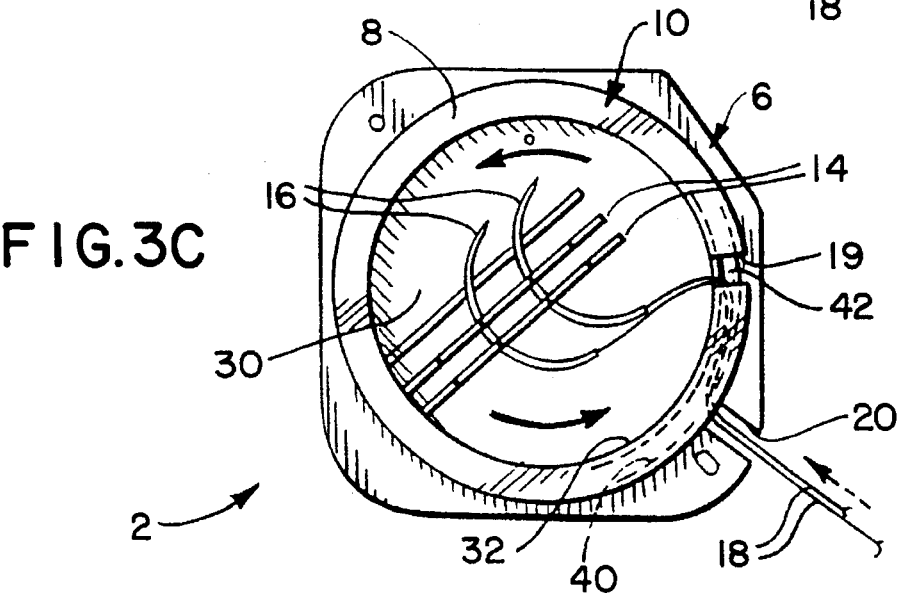

In one embodiment of the invention is illustrated in FIG. 3a–c the winding of a ligature into the inventive suture package is diagramed. A suture 18 with a needle 16 attached is placed in the needle park 14 mounted on base 10. The suture 18 is then placed in channel access port 19 that is in register with winding slot 20. Circular plate 10 is then rotated with respect to the flange member 6. As the circular plate 10 is rotated the suture 18 is pulled into the channel 42. After the suture is loaded into the channel 42 of the package 2, the flange member 6 and the circular plate 10 may be joined together.

Figure 4:
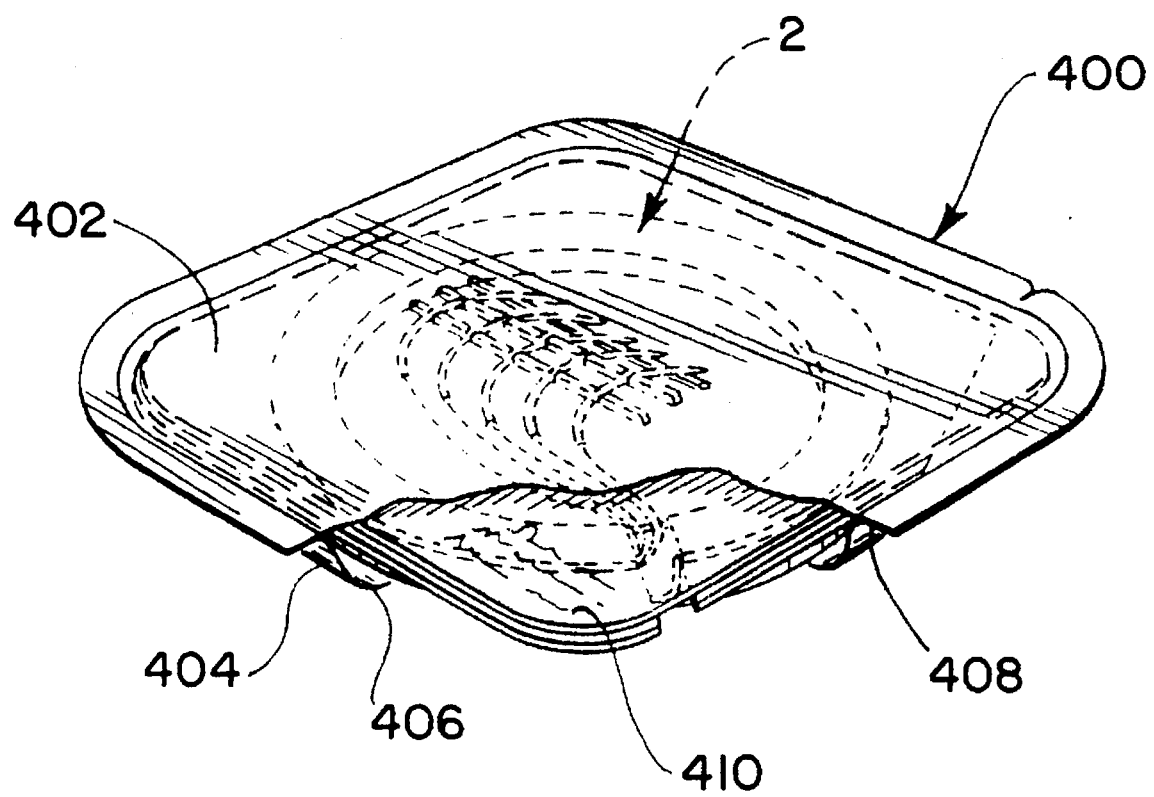
FIG. 4 illustrates the assembly of a suture package constructed in accordance with one embodiment of the present invention.

The flange member 6 may be joined together with the circular plate 10 using a variety of approaches such as adhesives, tapes etc. Preferably the flange and the circular plate will be formed of thermoplastic material that can be joined by melt fusing at least one region of the outer member 12 with the upper ring 8. Once the ligature package 2 is assembled, it may be placed inside an appropriate primary package and sterilized. One embodiment of a primary package design is provided in FIG. 4 and another suitable primary package is fully described in U.S. Pat. No. 4,424,898, which is hereby incorporated by reference herein.

The ligature package 2 is placed in a suitable primary package 400. The primary package 400 comprises a pair of substantially coextensive backing members 402 and a cover member 404. The cover member 404 is dished or hollowed 406 to accept the ligature package 2. The backing member 402 and/or the cover member 404 include a heat seal adhesive 408 about the periphery of their facing surface to seal the ligature package between the backing member 402 and cover member 404. The primary package 400 may also include a printed paper board member 410 that identifies the size and type of suture contained in the primary package 400. In this embodiment of the invention, it is preferred for the paper board member to be inside the primary package 400 and for the cover member 404 to be of a substantially transparent material to allow the paper board member 410 to be visible from the outside of the primary package 400.

We claim:

1. A package for retaining at least one ligature comprising a circular plate having a circular recessed base in a central portion thereof and a raised outer perimeter forming an inner wall that extends from and is substantially perpendicular to the base and an upper ring that extends from the inner wall and is substantially perpendicular to the inner wall and extends away from the base; and a flange member having a lower ring with an outer edge and an inner edge, extending from the outer edge is an outer wall which is substantially perpendicular to the lower ring, the outer wall having a top, extending from the top is an outer member that is substantially perpendicularly to the outer wall and extends from away from the lower ring; wherein the inner wall of the circular plate fits inside the inner edge of the lower ring and is adjacent thereto and the combination of the inner wall, lower ring, the outer wall and the upper ring defines a channel suitable for retaining a ligature said channel having an aperture for receiving said ligature.

2. The package of claim 1 wherein the channel is further defined by a lip that extends from the inner edge of the lower ring.

3. The package of claim 2 wherein there is additionally present a needle park mounted in the circular recessed base.

4. The package of claim 2 wherein additionally present within the channel is at least one ligature.

5. The package of claim 3 wherein additionally present is a suture attached to a needle and the needle is secured in the needle park and the suture is substantially retained in the channel.

6. The package of claim 4 wherein the circular plate has been joined to the flange.

7. The package of claim 6 wherein the ligature package is contained in a primary package.

8. The package of claim 6 wherein the package and ligature are sterile.

9. The package of claim 7 wherein the package, the needles and the suture are sterile.

10. A method of loading a suture attached to a needle into a package comprising securing a needle attached to a suture in a needle park in the package which is composed of a circular plate having a circular recessed base in the central portion thereof having the needle park mounted on said base and a raised outer perimeter forming an inner wall that extends from and is substantially perpendicular to the base and an upper ring that extends from the inner wall and is substantially perpendicular to the inner wall and extends away from the base; and a flange member having a lower ring with an outer edge and an inner edge, extending from the outer edge is an outer wall which is substantially perpendicular to the lower ring, the outer wall having a top, extending from the top is an outer member that is substantially perpendicularly to the outer wall and extends from away from the lower ring, the outer member having a winding slot therein; wherein the inner wall of the circular plate fits inside the inner edge of the lower ring and is adjacent thereto and the combination of the inner wall, lower ring, the outer wall and the upper ring defining a channel suitable for retaining a ligature said channel having an aperture for receiving said ligature;

placing a portion of the suture in the winding slot which is in register with the aperture to the channel; and rotating the circular plate relative to the flange member until the suture is drawn into the channel.

11. The method of claim 10 wherein the channel is further defined by a lip that extends from the inner edge of the lower ring.

12. The method of claim 10 wherein the package is thereafter sterilized.

13. The method of claim 10 wherein the package is thereafter placed in a primary package.

* * * * *